(12) United States Patent
Han et al.

(10) Patent No.: US 12,379,369 B2
(45) Date of Patent: Aug. 5, 2025

(54) NANOPORE DEVICE AND METHOD OF MANUFACTURING SAME

(71) Applicant: PALOGEN, INC., Palo Alto, CA (US)

(72) Inventors: Kyung Joon Han, San Jose, CA (US); Jungkee Yoon, Santa Clara, CA (US)

(73) Assignee: PALOGEN, INC., Palo Alto, CA (US)

( * ) Notice: Subject to any disclaimer, the term of this patent is extended or adjusted under 35 U.S.C. 154(b) by 711 days.

(21) Appl. No.: 17/747,420

(22) Filed: May 18, 2022

(65) Prior Publication Data

US 2022/0276219 A1    Sep. 1, 2022

Related U.S. Application Data

(63) Continuation of application No. 17/352,832, filed on Jun. 21, 2021, now Pat. No. 11,371,981, which is a
(Continued)

(51) Int. Cl.
| | | |
|---|---|---|
| B01L 3/00 | (2006.01) | |
| B01D 57/02 | (2006.01) | |
| B01D 67/00 | (2006.01) | |
| B01D 69/12 | (2006.01) | |
| B01D 71/02 | (2006.01) | |
| B01D 71/70 | (2006.01) | |
| B01F 33/302 | (2022.01) | |
| B01F 33/3033 | (2022.01) | |
| B01L 7/00 | (2006.01) | |
| B01L 9/00 | (2006.01) | |
| B65G 47/80 | (2006.01) | |
| B82B 1/00 | (2006.01) | |
| B82B 3/00 | (2006.01) | |
| B82Y 20/00 | (2011.01) | |
| B82Y 30/00 | (2011.01) | |
| B82Y 40/00 | (2011.01) | |
| C12M 1/34 | (2006.01) | |
| C12M 3/06 | (2006.01) | |

(Continued)

(52) U.S. Cl.
CPC ....... *G01N 33/48721* (2013.01); *B01D 57/02* (2013.01); *B01D 67/0034* (2013.01); *B01D 67/0062* (2013.01); *B01D 67/00791* (2022.08); *B01D 69/12* (2013.01); *B01D 71/0215* (2022.08); *B01D 71/022* (2013.01); *B01D 71/70* (2013.01); *B82B 1/001* (2013.01); *B82B 3/0014* (2013.01); *B82B 3/0019* (2013.01); *C12Q 1/6869* (2013.01); *B01D 2313/345* (2013.01)

(58) Field of Classification Search
None
See application file for complete search history.

(56) References Cited

FOREIGN PATENT DOCUMENTS

WO    WO-2017104398 A1 *   6/2017   .............. C12M 1/00

* cited by examiner

*Primary Examiner* — Jennifer Wecker
*Assistant Examiner* — Oyeleye Alexander Alabi
(74) *Attorney, Agent, or Firm* — Vista IP Law Group LLP

(57) ABSTRACT

A 3D nanopore device for characterizing biopolymer molecules includes a first selecting layer having a first axis of selection. The device also includes a second selecting layer disposed adjacent the first selecting layer and having a second axis of selection orthogonal to the first axis of selection. The device further includes an third electrode layer disposed adjacent the second selecting layer, such that the first selecting layer, the second selecting layer, and the third electrode layer form a stack of layers along a Z axis and define a plurality of nanopore pillars.

3 Claims, 10 Drawing Sheets

Related U.S. Application Data continuation of application No. 16/147,362, filed on Sep. 28, 2018, now Pat. No. 11,041,844.

(60) Provisional application No. 62/593,840, filed on Dec. 1, 2017, provisional application No. 62/566,313, filed on Sep. 29, 2017.

(51) Int. Cl.
| | |
|---|---|
| *C12N 1/14* | (2006.01) |
| *C12N 1/20* | (2006.01) |
| *C12Q 1/02* | (2006.01) |
| *C12Q 1/6848* | (2018.01) |
| *C12Q 1/686* | (2018.01) |
| *C12Q 1/6869* | (2018.01) |
| *G01N 15/10* | (2024.01) |
| *G01N 15/14* | (2024.01) |
| *G01N 15/1433* | (2024.01) |
| *G01N 21/29* | (2006.01) |
| *G01N 21/65* | (2006.01) |
| *G01N 33/487* | (2006.01) |
| *G01N 33/543* | (2006.01) |
| *G01N 33/574* | (2006.01) |
| *G01N 33/58* | (2006.01) |

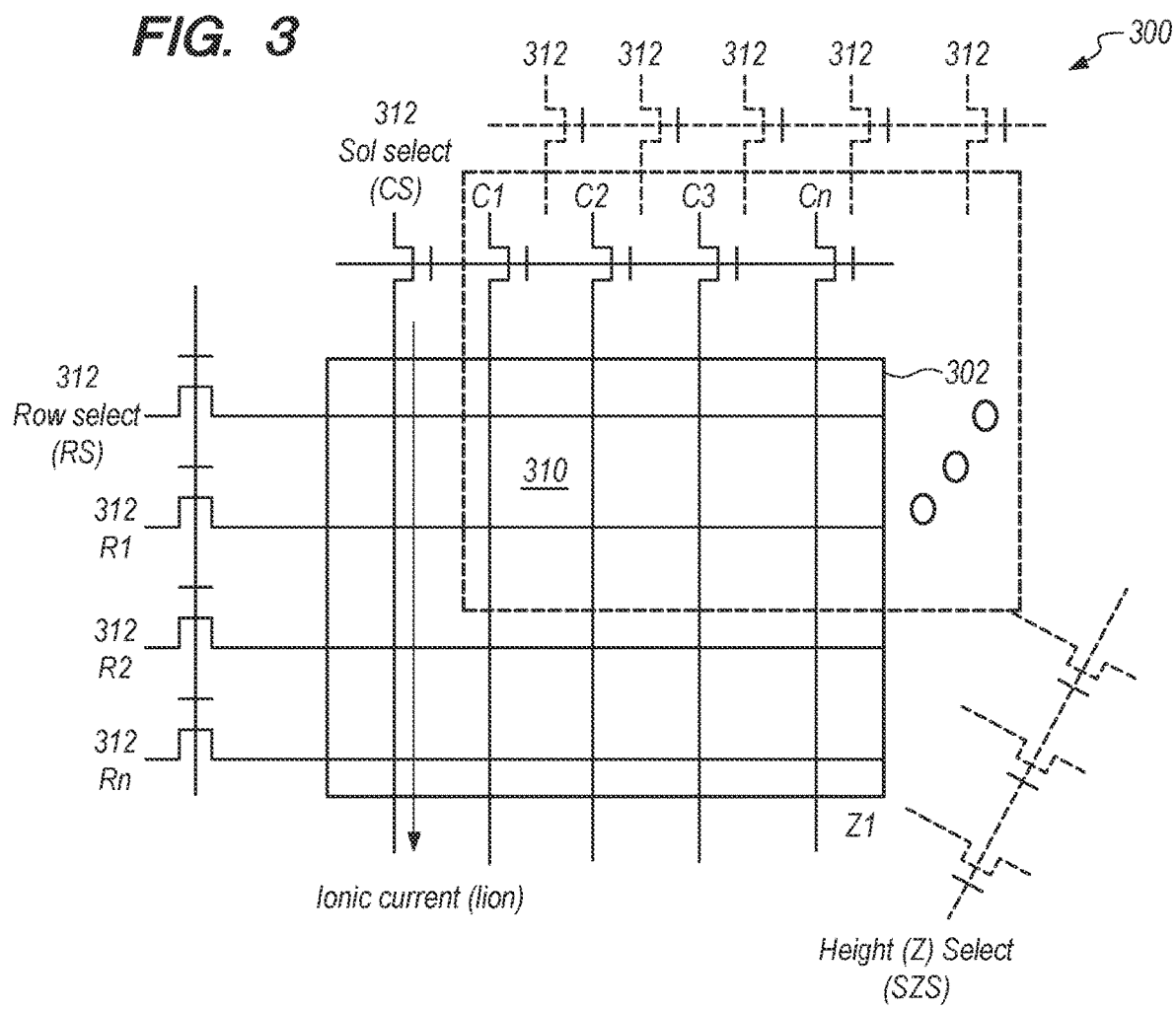

VPP=0V-3.3V, VCC=0V-2.8V, VSE=0.1V-1.5V,
other electrodes = GND unless specified otherwise

400

| SZS=VCC (selected plane), 0V (unselected plane) | | | |
|---|---|---|---|
| | | VR | VC |
| INHIBITORY OPERATION | V(SR/SC) | 0 | 0 |
| | V(SR/UC) | 0 | VPP |
| | V(UR/SC) | VPP | 0 |
| | V(UR/UC) | VPP | VCC |
| | | | |
| NORMAL OPERATION | V(SR/SC) | VPP | VPP |
| | V(SR/UC) | VPP | 0 |
| | V(UR/SC) | 0 | VPP |
| | V(UR/UC) | 0 | 0 |
| | | | |
| SENSING OPERATION | V(SR/SC) | VCC | VSE |
| | V(SR/UC) | VCC | 0 |
| | V(UR/SC) | 0 | 0 |
| | V(UR/UC) | 0 | 0 |

FIG. 4

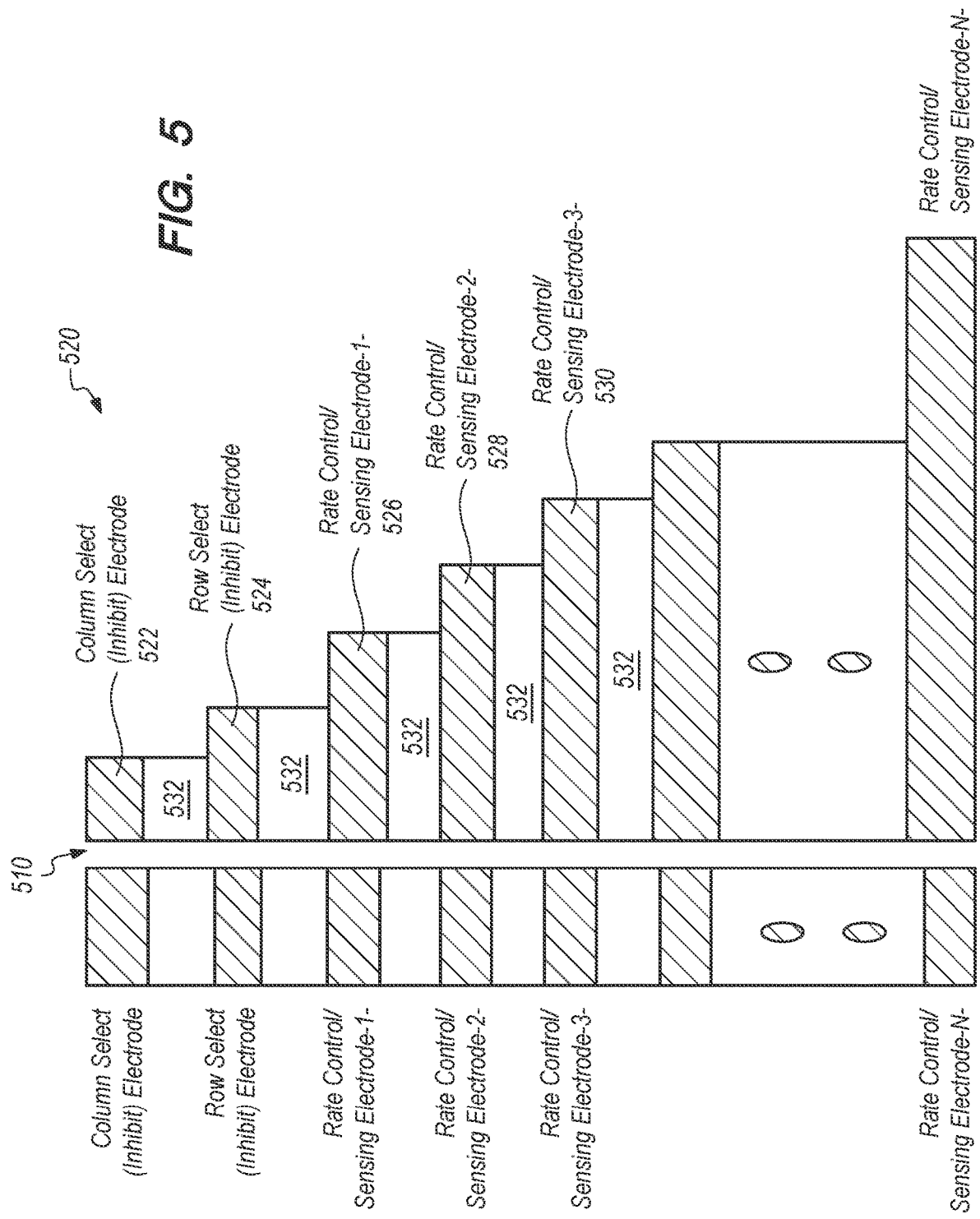

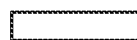 Si Dioxide
 Nitride
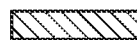 Metal/Poly
 Dielectric
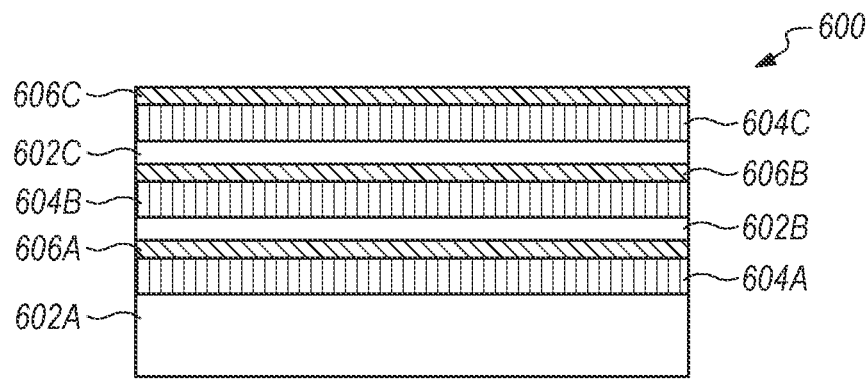
FIG. 6A
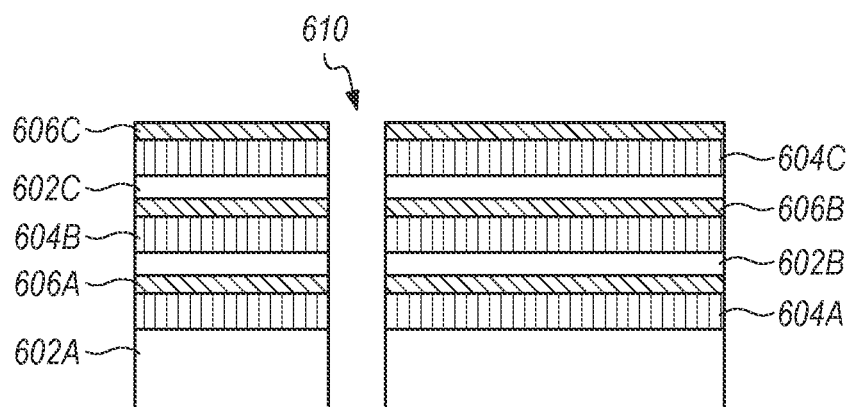
FIG. 6B
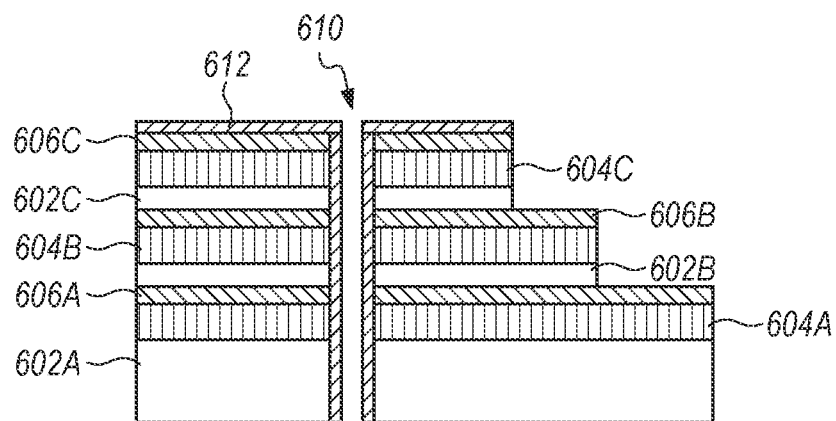
FIG. 6C

 Si Dioxide
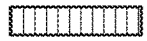 Nitride
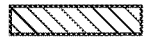 Metal/Poly
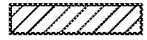 Dielectric
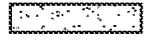 Substrate
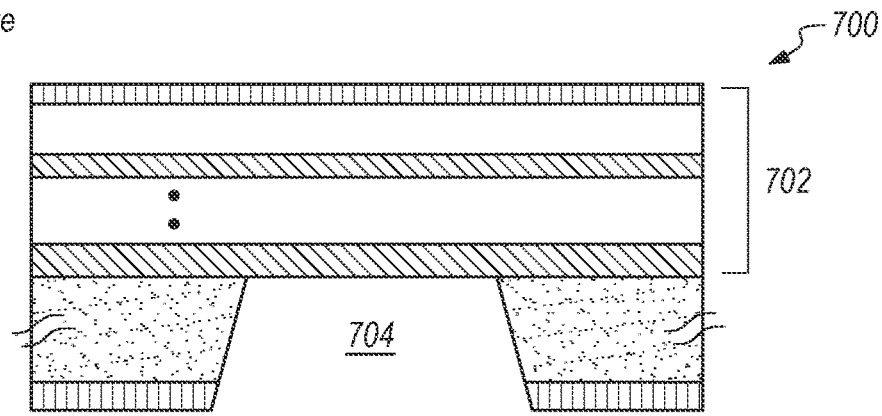
FIG. 7A
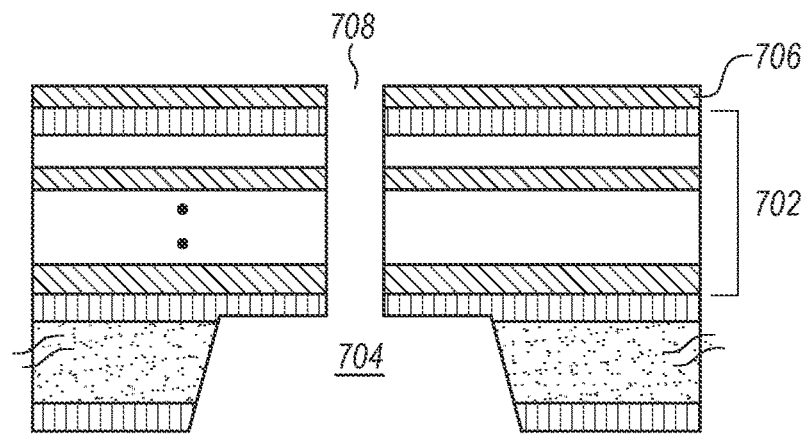
FIG. 7B
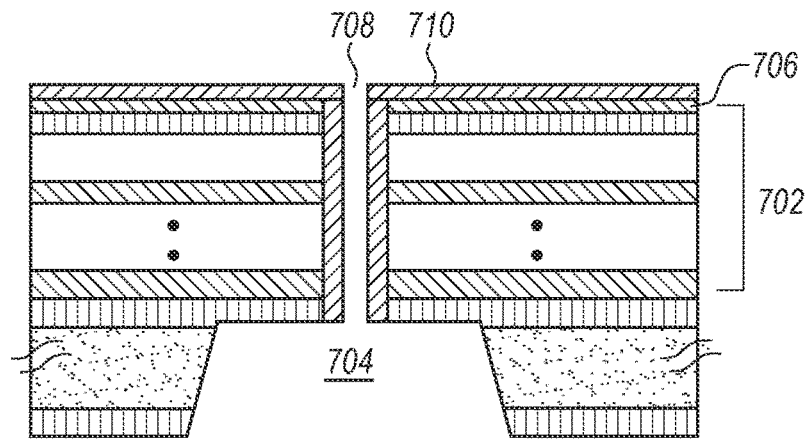
FIG. 7C

NANOPORE DEVICE AND METHOD OF MANUFACTURING SAME

CROSS-REFERENCE TO RELATED APPLICATION

The present application is a continuation of U.S. patent application Ser. No. 17/352,832, filed on Jun. 21, 2021, which is a continuation of U.S. patent application Ser. No. 16/147,362, filed on Sep. 28, 2018, which claims priority to U.S. Provisional Patent Application Ser. No. 62/566,313, filed on Sep. 29, 2017 and entitled "MANUFACTURE OF THREE DIMENSIONAL NANOPORE DEVICE," and U.S. Provisional Patent Application Ser. No. 62/593,840, filed on Dec. 1, 2017 and entitled "NANOPORE DEVICE AND METHOD OF MANUFACTURING SAME." This application includes subject matter similar to the subject matter described in co-owned U.S. Provisional Patent Application Ser. No. 62/612,534, filed on Dec. 31, 2017 and entitled "NANOPORE DEVICE AND METHODS OF ELECTRICAL ARRAY ADDRESSING AND SENSING," U.S. Provisional Patent Application Ser. No. 62/628,214, filed on Feb. 8, 2018 and entitled "BIOMEMORY FOR NANOPORE DEVICE AND METHODS OF MANUFACTURING SAME," and U.S. Provisional Patent Application Ser. No. 62/711,234, filed on Jul. 27, 2018 and entitled "NANOPORE DEVICE AND METHODS OF DETECTING CHARGED PARTICLES USING SAME." The contents of the foregoing applications and patents are hereby fully incorporated by reference into the present application in their entirety.

FIELD OF THE INVENTION

The present invention relates generally to systems, devices, and processes for characterizing biopolymer molecules, and methods of manufacturing such systems and devices.

BACKGROUND

Nucleic acid (e.g., DNA, RNA, etc.) sequencing is one of the most powerful methods to identify genetic variations at the molecular level. Many signatures of genetic diseases can be diagnosed by information collected through genome-wide single nucleotide polymorphisms ("SNPs") analysis, gene fusion, genomic insertion and deletion, etc. These techniques and other molecular biology techniques require nucleic acid sequencing at some point. Current technologies to sequence nucleic acids at the single molecule level include a nanopore sequencing technology that has advantages over previous sequencing techniques because nanopore sequencing technology has the characteristics of a label-free and amplification-free technique that also has improved read lengths, and improved system throughput. Accordingly, nanopore sequencing technology has been incorporated into high-quality gene sequencing applications.

Early experimental systems for nanopore based DNA sequencing detected electrical behavior of ssDNA passing through an α-hemolysin (αHL) protein nanopore. Since then, nanopore based nucleic acid sequencing technology has been improved. For instance, solid-state nanopore based nucleic acid sequencing replaces biological/protein based nanopores with solid state (e.g., semiconductor, metallic gates) nanopores, as described below.

A nanopore is a small hole (e.g., with a diameter of about 1 nm to about 1000 nm) that can detect the flow of electrons through the hole by the change in the ionic current and/or tunneling current. Because each nucleotide of a nucleic acid (e.g., adenine, cytosine, guanine, thymine in DNA, uracil in RNA) affects the electric current density across the nanopore in a specific manner as it physically passes through the nanopore, measuring changes in the current flowing through a nanopore during translocation results in data that can be used to directly sequence a nucleic acid molecule passing through the nanopore. As such, Nanopore technology is based on electrical sensing, which is capable of detecting nucleic acid molecules in concentrations and volumes much smaller than that required for other conventional sequencing methods. Advantages of nanopore based nucleic acid sequencing include long read length, plug and play capability, and scalability. However, current biological nanopore based nucleic acid sequencing techniques can require a fixed nanopore opening (e.g., with a diameter of about 2 nm), have poor sensitivity (i.e., unacceptable amount of false negatives), high cost that renders production worthy manufacturing a challenge, and strong temperature and concentration (e.g., pH) dependency.

With advancements in semiconductor manufacturing technologies, solid-state nanopores have become an inexpensive and superior alternative to biological nanopores partly due to the superior mechanical, chemical and thermal characteristics, and compatibility with semiconductor technology allowing the integration with other sensing circuitry and nanodevices. However, current nanopore DNA sequencing techniques (e.g., involving biological and/or solid-state nanopores) continue to suffer from various limitations, including low sensitivity and high manufacturing cost. FIG. 1 schematically depicts a state-of-art solid-state based 2-dimensional ("2D") nanopore sequencing device 100. While, the device 100 is referred to as "two dimensional," the device 100 has some thickness along the Z axis.

Many of the limitations of nanopore DNA sequencing techniques result from the intrinsic nature of nanopore devices and techniques that must overcome the fast translocation speed and small size (e.g., height of about 0.34 nm and diameter of about 1 nm) of a single nucleotide. Conventional electronic instrumentation (e.g., nano-electrodes) cannot resolve such fast moving and small nucleotides using conventional nanopore based DNA sequencing techniques. Also high manufacturing cost prevents wider applications of nanopore based DNA sequencing.

Many efforts have been made to overcome these drawbacks, including the use of many different types of biological, solid-state and hybrid (biological and solid-state) nanopores and nanopore sensors. However, none of these efforts has been successful in mass production.

There is a need for nanopore based sequencing systems and devices that address the shortcomings of currently-available configurations. In particular, there is a need for nanopore based sequencing systems and devices with acceptable sensitivity and manufacturing cost.

SUMMARY

Embodiments described herein are directed to nanopore based sequencing systems and methods of manufacturing same. In particular, the embodiments are directed to 3D nanopore based sequencing systems and methods of manufacturing same.

In one embodiment, a 3D nanopore device for characterizing biopolymer molecules includes a first selecting layer having a first axis of selection. The device also includes a second selecting layer disposed adjacent the first selecting layer and having a second axis of selection orthogonal to the first axis of selection. The device further includes an third electrode layer disposed adjacent the second selecting layer, such that the first selecting layer, the second selecting layer, and the third electrode layer form a stack of layers along a Z axis and define a plurality of nanopore pillars.

In one or more embodiments, the first selecting layer includes a first plurality of inhibitory electrodes. The second selecting layer may include a second plurality of inhibitory electrodes. The first and second pluralities of inhibitory electrodes may form an array partially defining the plurality of nanopore pillars therein. The third electrode layer may include an electrode configured to modulate an electrical bias and to detect a current modulation. The device of may also include one or more electrode layers disposed adjacent the third electrode layer.

In one or more embodiments, the device also includes a top chamber disposed adjacent the first selecting layer. The device further includes a bottom chamber disposed adjacent a bottom electrode layer, such that the plurality of nanopore pillars fluidly couple the top and bottom chambers and provide a translocation channel when multi-electrodes are present in the device. The device may also include an electrolyte solution in the top and bottom chambers and surrounding the first selecting layer, the second selecting layer, and the third electrode layer. The electrolyte solution may include KCl or $LiCl_2$.

In one or more embodiments, the third electrode layer includes a metal rate-control electrode. The third electrode layer may include metals, such as Ta, Al, Cr, Au—Cr, Ti, Graphene, or Al—Cu. The third electrode may include highly doped (either n+ or p+ type) polysilicon or salicided polysilicon. The third electrode layer may have a thickness from 0.2 nm to 1000 nm. The third electrode layer may include a sensing electrode. The sensing electrode may operate by ion blockade, tunneling, capacitive sensing, piezoelectric, or microwave-sensing.

In one or more embodiments, the device also includes an inner membrane layer configured to modify an inner diameter of the plurality of nanopores. The inner membrane layer may include low stress silicon rich nitrides, such as $Si_3N_4$ and is coated with dielectrics, such as $Al_2O_3$, $SiO_2$, ZnO, or $HfO_2$. The inner membrane layer may have a thickness of about 10 nm to about 50 nm. Each of the plurality of nanopores may have respective diameters from about 0.2 nm to about 1000 nm. The device may also include a top membrane layer. The top membrane layer may include $Si_3N_4$, $Al_2O_3$, $SiO_2$, 2D dielectrics (e.g., MoS2 or hBN), and polymer membranes (e.g., polyimide and PDMS). The top membrane layer may have a thickness of about 5 nm to about 50 nm.

In another embodiment, a method of manufacturing a 3D nanopore device includes depositing a first $Si_3N_4$ layer on the first Si substrate or the first dielectric base layer. The method includes depositing a first dielectric layer on the first $Si_3N_4$ layer. The method also includes depositing a first metal or polysilicon layer on the first dielectric layer. In one or more embodiments, the method also includes etching and patterning the first metal or polysilicon electrode layer. The method also includes depositing a second dielectric layer on the patterned first metal or polysilicon electrode layer.

The method also includes depositing a second metal or polysilicon layer on the first metal or polysilicon electrode layer. The method further includes depositing a second $Si_3N_4$ layer on a second dielectric layer. In one or more embodiments, the method also includes etching and patterning the second metal or polysilicon electrode layer. The method further includes depositing and patterning the multiple layers of metal or polysilicon electrode layers.

The method includes etching the first Si or dielectric substrate base layer from the backside to create a channel from the backside.

The method includes a patterning the nanopore channel from the surface on the multiple stack of $Si_3N_4$ layers, dielectric layer, and metal or polysilicon layers to form a nanopore therethrough. The method may also include disposing each metal or polysilicon electrodes in every channel and electrically coupling the metal or polysilicon electrode layers.

In one or more embodiments, the method also includes etching a second channel into the bottom $Si_3N_4$ layer, where the first and second channels are orthogonal to each other. The method may also include disposing a second inhibitory electrode in the second channel and electrically coupling the second inhibitory electrode to the bottom $Si_3N_4$ layer. The method may also include depositing a third dielectric base layer on the second metal layer, and etching the third dielectric base layer to form the nanopore therethrough. The method may also include etching the third dielectric layer, and electrically coupling a third electrode to the third dielectric layer. The method may also include etching a substrate, and fluidly coupling a bottom chamber to the plurality of nanopore pillars.

In one or more embodiments, the method also includes disposing the first dielectric base layer, the first $Si_3N_4$ layer, and the first metal in a middle chamber between top and bottom chambers, where the top, middle, and bottom chambers contain an electrolyte solution, such that the top and bottom chambers are fluidly coupled by the nanopore. Deposition of the first $Si_3N_4$ layer, the first metal layer, and the dielectric coating layer may use ALD or CVD. Etching the first dielectric base layer, the first $Si_3N_4$ layer, and the first metal layer to form the nanopore may use high aspect ratio etching.

In still another embodiment, a method of detecting a charged particle uses a 3D nanopore device having top, middle and bottom chambers, and a 3D nanopore array disposed in the middle chambers such that the top and bottom chambers are fluidly coupled by a plurality of nanopores in the 3D nanopore array. The method includes adding electrolyte solution including the charged particle to the top, middle, and bottom chambers. The method also includes placing top and bottom electrodes in the top and bottom chambers respectively. The method further includes applying an electrophoretic bias between the top and bottom electrodes. Moreover, the method includes applying first and second selection biases to first and second selection electrodes in the 3D nanopore device to select one or more nanopores of the plurality of nanopores through which the charged particle will be directed. In addition, the method includes applying a rate control bias to a rate control electrode in the 3D nanopore device to modulate a translocation rate of the charged particle through the one or more nanopores. The method also includes applying a sensing bias to a sensing electrode in the 3D nanopore device. The method further includes detecting a change in a current in the sensing electrode.

In one or more embodiments, the current is an electrode current or a tunneling current.

In yet another embodiment, a method of manufacturing a sensor including a 3D nanopore channel pillar array, a plurality of electrodes, a top chamber, and a bottom chamber, includes placing the 3D nanopore channel pillar array in an electrolyte solution including biomolecules and DNA.

The method also includes placing an electrode in the electrolyte. The method further includes applying a bias to the electrode in the electrolyte. Moreover, the method includes placing cross patterned column and row inhibitory electrodes surrounding nanopore pillars on top of the 3D nanopore channel pillar array. In addition, the method includes placing metal plane electrodes surrounding the nanopore pillars in the 3D nanopore channel pillar array, the metal plane electrodes including a rate-control electrode and a sensing electrode. The method also includes applying a rate-control bias in the rate-control electrode. The method further includes applying a sensing bias in the sensing electrode. Moreover, the method includes detecting a change in an electrode current in the electrolyte. In addition, the method includes detecting a change in a tunneling current in the electrodes.

In one or more embodiments, the rate-control electrode has a thickness ranges from about 2 nm to about 1000 nm. The rate-control electrode may include Ta, Cr, Al, Au—Cr, Graphene, or Al—Cu. It may include heavily doped (n- or p-type) polysilicon or salicided polysilicon. The 3D nanopore channel pillar array may include a biological layer having the rate-control electrode, such that the 3D nanopore channel pillar array is a hybrid. The top and bottom chambers may contain at least some of the electrolyte solution. The electrolyte solution may include KCl and $LiCl_2$. The electrodes for top and bottom chamber may include $Ag/AgCl_2$. The cross patterned column and row inhibitory electrodes may enable array operation by selecting and deselecting the column and row by applying an inhibitory bias to stop ionic current flow vertically. The sensing electrode may utilize ion blockade sensing, tunneling sensing, capacitive sensing, piezoelectric sensing, and/or wave-sensing.

In one or more embodiments, the 3D nanopore channel pillar array includes a plurality of dielectric-electrodes in a dielectric-electrode stack. The dielectric-electrode stack includes a membrane layer, a dielectric layer to modify a nanopore channel opening width, an array of nanopore channel pillars, a stack of rate-control dielectric-electrode layers, a stack of sensing dielectric-electrode layers, and a source select dielectric-electrode layer. The membrane layer may include a dielectric material and have a thickness from about 10 nm to about 50 nm. The dielectric material may be $Si_3N_4$, $Al_2O_3$, or $SiO_2$. The membrane layer may modify the nanopore channel opening width. The nanopore channel opening width may be from about 2 nm to about 100 nm patterned by standard optical lithography and ion beam (e.g., FIB, TEM) techniques.

In one or more embodiments, the 3D nanopore channel pillar array is manufactured using ALD and/or CVD deposition of dielectric layers, High aspect ratio Reactive Ion Etch deep trench process (nanopore channel opening etch), ALD and/or CVD deposition of trimming dielectric layers, and/or ALD and/or CVD deposition of membrane dielectric layers.

In one or more embodiments, the dielectric-electrode stack also includes a bottom dielectric layer. The bottom dielectric layer may have a thickness of about 100 nm to 1000 nm. The bottom dielectric layer may include $SiO_2$, glass, or SOI to reduce substrate coupled low level noise. The dielectric-electrode stack may also include a top dielectric layer. The top dielectric layer may have a thickness of about 5 nm to about 50 nm. The top dielectric layer may include $SiO_2$, $Si_3N_4$, or $Al_2O_3$. The top dielectric layer may determine a final nanopore channel opening width.

In one or more embodiments, the method also includes forming a nanopore channel pillar using high aspect ratio etching to provide a sharp shape to a trench profile of the nanopore channel pillar. The high aspect ratio etching may have an aspect ratio of greater than 5.

In one or more embodiments, the 3D nanopore channel pillar array facilitates multiplex sequencing applications using high density low cost nanopore channels. A number of electrodes in the 3D nanopore array may be selected depending on the required sequencing applications to provide a Time of Flight ("TOF") technique to control a translocation speed by controlled biasing. Controlling the translocation speed may improve reading of DNA molecules and improves a sensitivity of the sensor.

In one or more embodiments, the 3D nanopore channel pillar array is integrated in a CMOS flow, thereby facilitating embedded biosensor solutions for CMOS technology. The CMOS flow may include a 2-dim well for electrochemical reactions. The CMOS flow may include an ion-sensitive filed effect transistor technology.

In one or more embodiments, the 3D nanopore channel pillar array incorporates a hybrid type of nanopore technology including a biological component and a solid-state component in a 3D configuration. The 3D nanopore channel pillar array may facilitate an electro-chemical, thermal, or electro-optical reaction to take place in an enlarged, separated nanopore well with a multi-electrode system to enhance electrochemical and/or sequencing reactions. The 3D nanopore channel pillar array may facilitate multiplex sequencing using a multi-array configuration where individual nanopore channel pillars are addressable. The 3D nanopore channel pillar array may facilitate standard qPCR within a nanopore channel pillar. The 3D nanopore channel pillar array may facilitate probe-mediated targeted sequencing. The 3D nanopore channel pillar array may facilitate tuning of a nanopore channel opening width for different applications.

In one or more embodiments, the nanopore channel opening width is tunable from about 1 nm to about 100 nm. The nanopore channel opening width may be electronically tunable during manufacturing.

In one or more embodiments, the method also includes forming a hybrid nanopore channel to enhance stability of the sensor. Forming the hybrid nanopore may include inserting a stable biological component to construct a semi-synthetic membrane porin. The stable biological component may be an αHL molecule. The αHL molecule may be inserted into a SiN based 3D nanopore.

In one or more embodiments, the method also includes using a top inhibitory electrode to induce a structure in the stable biological component to ensure alignment of the stable biological component and hybrid nanopore.

The aforementioned and other embodiments of the invention are described in the Detailed Description which follows.

BRIEF DESCRIPTION OF THE DRAWINGS

The foregoing and other aspects of embodiments are described in further detail with reference to the accompanying drawings, in which the same elements in different figures are referred to by common reference numerals, wherein:

FIG. 3 schematically illustrates a 3D nanopore device according to one embodiment including some details of its operation.

FIG. 4 is a table summarizing the voltage operation of the nanopore device depicted in FIG. 3.

FIG. 5 schematically illustrates a 3D nanopore device according to one embodiment including some of the electrodes therein.

FIGS. 6A-6E illustrate a method for manufacturing a 3D nanopore device according to one embodiment.

FIGS. 7A-7E illustrate a method for manufacturing a 3D nanopore device according to another embodiment.

Figure 1:
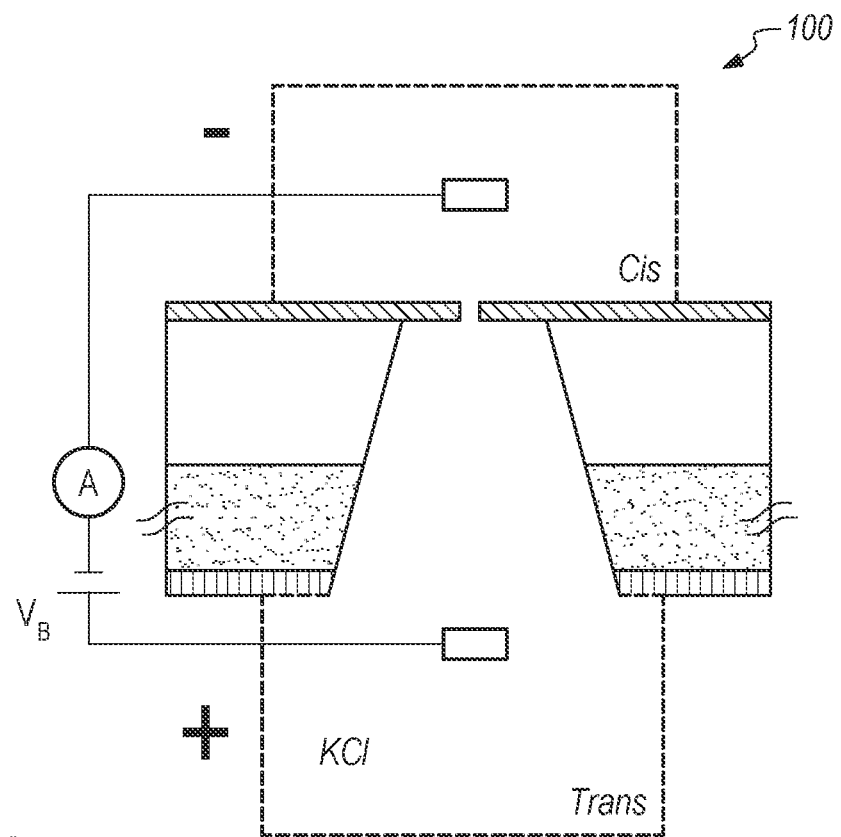
FIG. 1 schematically illustrates a prior art solid-state 2D nanopore device.

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Exemplary Nanopore Devices

As described above, current state-of-art nanopore devices are limited at least in terms of sensitivity and manufacturing cost. The nanopore device embodiments described herein address, inter alia, these limitations of current nanopore devices.

Figure 2A:
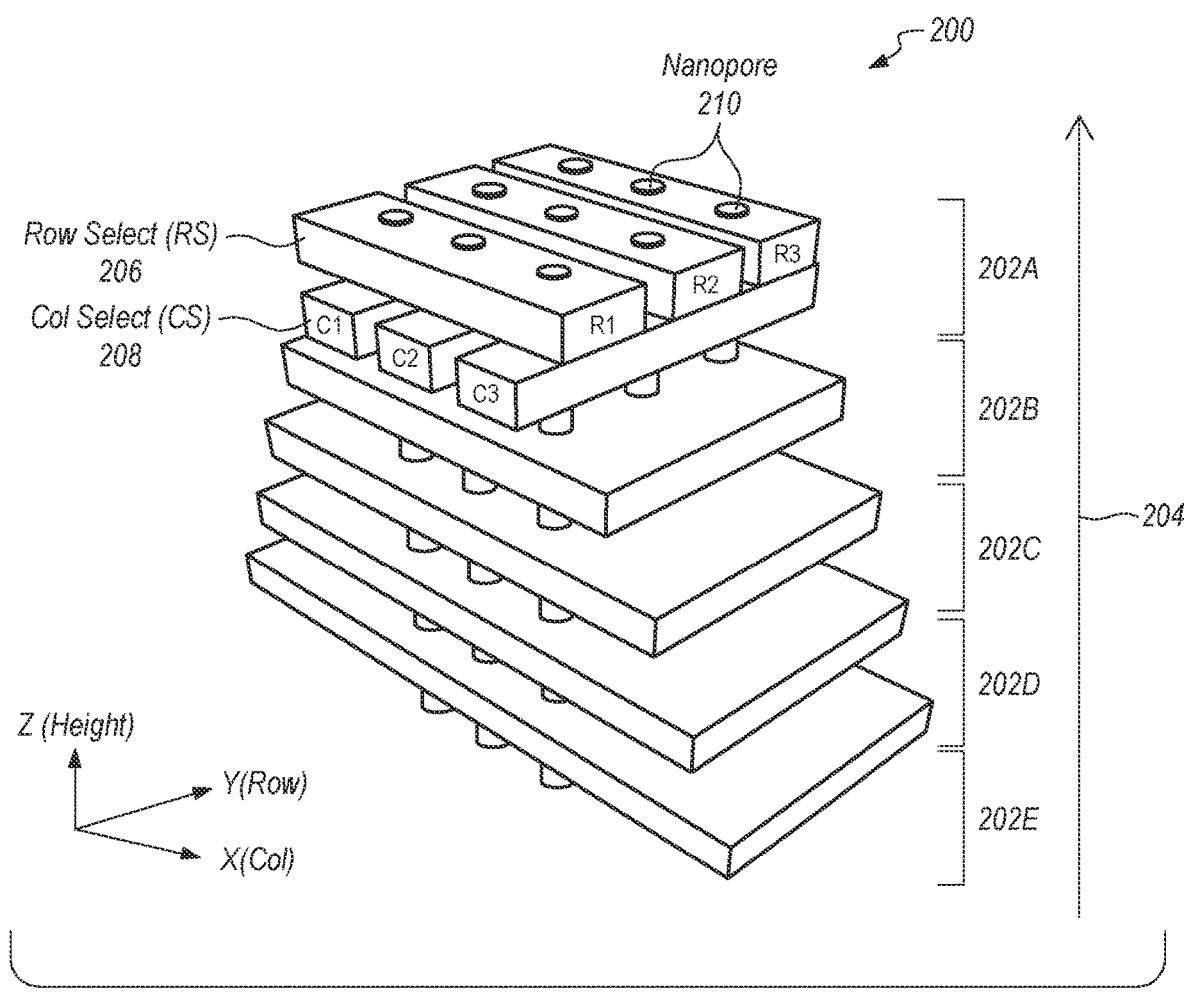
FIGS. 2A-2D schematically illustrate a 3D nanopore device according to one embodiment from perspective, top, front, and right views, respectively.
Figure 2B:
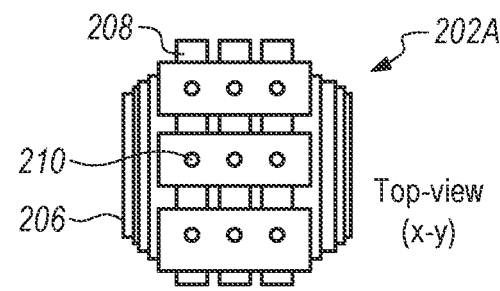
Figure 2C:
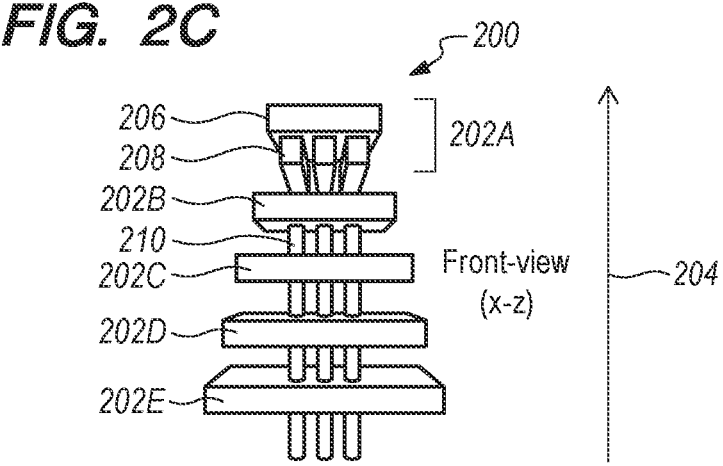
Figure 2D:
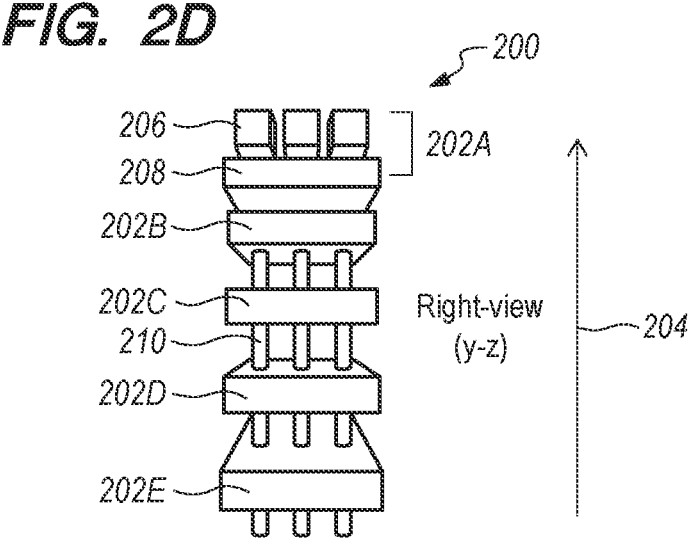

FIG. 2A-2D schematically depict various views of a nanopore device 200 incorporating solid-state nanopore technology with a three dimensional ("3D") array architecture according to one embodiment. As shown in FIG. 2A, the device 200 includes a plurality of 2D arrays or layers 202A-202E stacked along a Z axis 204. While the 2D arrays 202A-202E are referred to as "two dimensional," each of the 2D arrays 202A-202E has some thickness along the Z axis. FIG. 2B depicts a top view of the top 2D array 202A depicted in FIG. 2A. FIGS. 2C and 2D schematically depict front and right side views of the nanopore device 200 depicted in FIG. 2A.

The top 2D array 202A includes first and second selecting (inhibitory electrode) layers 206, 208 configured to direct movement of charged particles (e.g., biopolymers) through the nanopores 210 (pillars) formed in the first and second selecting layers 206, 208. The first selecting layer 206 is configured to select from a plurality of rows (R1-R3) in the 2D array 202A. The second selecting layer 208 is configured to select from a plurality of columns (C1-C3) in the 2D array 202A. In one embodiment, the first and second selecting layers 206, 208 select from the rows and columns, respectively, by modifying a charge adjacent the selected row and column and/or adjacent to the non-selected rows and columns. The other 2D arrays 202B-202E include rate control/current sensing electrodes. Rate control electrodes may be made of highly conductive metals, such as Au—Cr, TiN, TaN, Pt, Cr, Graphene, Al—Cu, etc. The rate control electrodes may have a thickness of about 2 to about 1000 nm. Rate control electrodes may also be made in the biological layer in hybrid nanopores.

Hybrid nanopores include a stable biological/biochemical component with solid state components to form a semi-synthetic membrane porin to enhance stability of the nanopore. For instance, the biological component may be an αHL molecule. The αHL molecule may be inserted into a SiN based 3D nanopore. The αHL molecule may be induced to take on a structure to ensure alignment of the αHL molecule with the SiN based 3D nanopore by apply a bias to an electrode (e.g., in the top 2D array 202A).

The nanopore device 200 has a 3D vertical pillar stack array structure that provides a much larger surface area for charge detection than that of a conventional nanopore device having a planar structure. As a charged particle (e.g., biopolymer) passes through each 2D array 202A-202E in the device, its charge can be detected with a detector (e.g., electrode) in some of the 2D arrays 202B-202E. Therefore, the 3D array structure of the device 200 facilitates higher sensitivity, which can compensate for a low signal detector/electrode. Further, the highly integrated small form factor 3D structure provides a high density nanopore array while minimizing manufacturing cost.

In use, the nanopore device 200 is disposed in a middle chamber separating top and bottom chambers (not shown) such that the top and bottom chambers are fluidly coupled by the nanopore pillars 210. The top, middle, and bottom chambers include an electrolyte solution (e.g., Ag, $AgCl_2$, etc.) containing the charged particles (e.g., DNA) to be detected. Different electrolyte solutions can be used for the detection of different charged particles.

Electrophoretic charged particle translocation can be driven by applying a bias to electrodes disposed in a top chamber (not shown) adjacent the top 2D array 202A of the nanopore device 200 and a bottom chamber (not shown) adjacent the bottom 2D array 202E of the nanopore device 200. In some embodiments, the nanopore device 200 is disposed in a middle chamber (not shown) such that the top and bottom chambers are fluidly and electrically coupled by the nanopore pillars 210 in the nanopore device 200. The top, middle, and bottom chambers may contain the electrolyte solution.

FIG. 3 schematically depicts a nanopore device 300 according to another embodiment. FIG. 3 depicts the top 2D array 302 in a cross-sectional (x-z plane) view showing the 3D nanopore 310 and nano-electrode schemes. Each nanopore 310 is surrounded by nano-electrodes 312, allowing the nanopore 310 channel to operate under an electric bias field condition generated using the nano-electrodes 312. Cross-patterned nanogap nano-electrodes 312CS-312Cn, 312RS-312Rn are disposed in two layers on top of the nanopore device 300. These nano-electrodes 312CS-312Cn, 312RS-312Rn are column and row inhibitory nano-electrodes 312CS-312Cn, 312RS-312Rn for the nanopore array, respectively. The cross-patterned nano-electrodes 312CS-312Cn, 312RS-312Rn as shown in the top 2D array 302 (x-y plane view) may be formed/patterned at the metal lithography steps. Nano-electrodes 312 in the remaining 2D arrays in the 3D stack may be formed by plane depositing metals. The nanopore 310 hole pillars are surrounded by the metal nano-electrodes 312CS-312Cn, 312RS-312Rn, and thus may operate under the full influence of the electrical bias applied to the multiple stacked nano-electrodes 312.

By applying an inhibitory electrical bias (0V-VCC) to select nanogap nano-electrodes 312CS-312Cn, 312RS-312Rn in the top 2D array 302, biomolecular translocation (e.g., electrophoretic) through one or more nanopores 302 in the top 2D nanopore array 302 can be inhibited to control nanopore array operation according to one embodiment. The electrical bias applied to the nano-electrodes 312CS-312Cn, 312RS-312Rn can generate an electric field sufficient to suppress ionic translocation of charged particles (e.g., nucleic acids) from a top chamber (not shown) to a bottom chamber (not shown) in a direction orthogonal to the nano-electrodes 312CS-312Cn, 312RS-312Rn. Nano-electrode 312 mediated ionic translocation suppression can be substantially complete or the electrical bias can be modulated to only reduce the rate of ionic translocation. In one embodiment, after one or more nanopores 310 are selected (e.g., for DNA biomolecules translocation and sequencing), the electrical biases in a stack of 3D nanopore nano-electrodes 312 can be modulated to control the biomolecular translocation speed. In one embodiment, the inhibitory electrical bias reduces/stops ionic current flow in the vertical direction to thereby select and/or deselect various columns and rows defined by the nanogap nano-electrodes 312CS-312Cn, 312RS-312Rn. At the same time, the nano-electrodes 312 can detect current modulations resulting from passage of charged particles (e.g., DNA biomolecules) through the 3D vertical nanopore 310 pillars. In some embodiments, the nano-electrodes 312 can detect current modulations using a variety of principles, including ion blockade, tunneling, capacitive sensing, piezoelectric, and microwave-sensing.

FIG. 4 is a table 400 illustrating the voltage operation of the nanopore device 300 depicted in FIG. 3. As shown in FIG. 4, the nanopore device 300 can be operated in both translocation and read (sense) mode by modulating the voltage applied to various electrodes 312.

FIG. 5 schematically illustrates a single 3D nanopore sensor 520 in a nanopore device according to one embodiment. The sensor 520 has a column inhibitory electrode layer 522, a row inhibitory electrode layer 524, and a plurality of rate control/sensing electrode layers 526, 528, 530. These layers are stacked on top of each other and separated by an insulator layer 532 (e.g., $SiO_2$) to define a vertical nanopore 510 hole pillar. Each layer may have a polysilicon or metal (e.g., Ta, Al, Cr, Au—Cr, Ni, Graphene, etc.) top sub-layer and various other sub-layers (e.g., $Al_2O_3$, $Si_3N_4$, $n^+$ or $p^+$ polysilicon, etc.) The 3D nanopore sensor 520 can operate on a variety of principles, including ion blockade, tunneling, capacitive sensing, piezoelectric, and microwave-sensing. Rate control/sensing electrode layers 526, 528, 530 can be activated by applying a rate control or a sensing bias to the respective electrode layers 526, 528, 530. The sensing electrode layers 526, 528, 530 can detect a change in an electrical characteristic (e.g., an electrode current and/or a tunneling current).

3D nanopore devices (e.g., 200, 300) allow either direct or targeted sequencing in an array while minimizing form-factor overhead, because the 2D arrays 202, 302 in the nanopore devices 200, 300 can be stacked vertically instead of positioned horizontally, thereby allowing for high density applications. Further, 3D nanopore devices (e.g., 200, 300) are scalable, with medium to large 3D nanopore devices having more than 1,000 nanopore 210, 310 pillars. Consequently, a larger number of sequencing sensors can be accommodated within the same form-factor. 3D nanopore devices (e.g., 200, 300) can also incorporate biological nanopore or hybrid nanopore technologies to provide more architectural flexibility to accommodate a user's needs.

In 3D nanopore devices (e.g., 300), each nanopore 310 pillar is composed of a stack of nano-electrodes 312 defining a plurality of nanopores 310. As such, the effective surface area of the sensors in each nanopore 310 column can be orders of magnitude greater than the surface area of a single sensor. In one embodiment, the effective sensor surface area can be 2-3 orders of magnitude greater than the surface area of a single sensor. This increase in effective sensor surface area can significantly improve the sensor signal to noise ratio and sensitivity, while minimizing manufacturing costs.

Exemplary Nanopore Device Manufacturing Methods 3D nanopore devices (e.g., 200, 300) can be manufactured utilizing many different methods. In one embodiment, a semiconductor technology (e.g., CMOS process, described below) is used to manufacture 3D nanopore devices 200, 300. The CMOS process also allows nanopore 310 width to be tunable using a large nanopore array. In one embodiment, nanopore 310 width can be controlled during manufacturing using software with a look up table, allowing for mass production manufacturing. Using a CMOS process can embed biosensor solutions in CMOS technology. In various embodiments, the CMOS process includes a 2-dim well for electrochemical reactions and/or an ion-sensitive filed effect transistor technology. Microfluidic channels can be integrated into the 3D nanopore devices 200, 300 (e.g., within a die), therefore reducing the cost of the devices 200, 300.

Figure 6D:
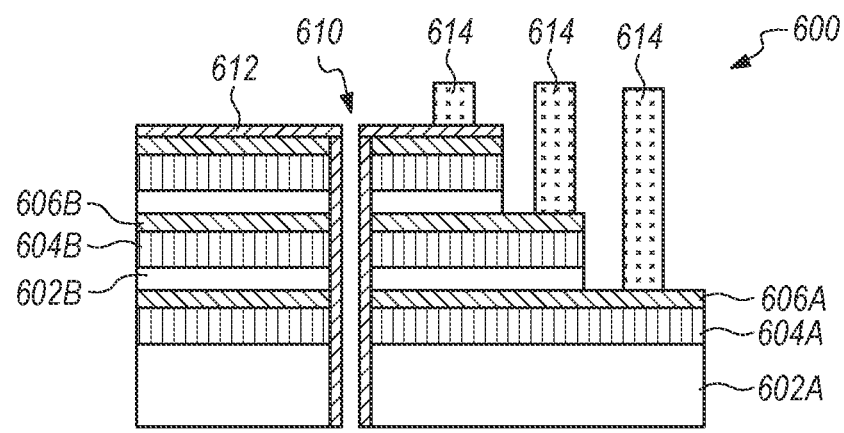

FIGS. 6A-6E illustrate a method 600 of manufacturing a nanopore device according to one embodiment. As shown in FIG. 6A, a first dielectric base layer (e.g., $SiO_2$, $Al_2O_3$, etc.) 602A, a first base layer of $Si_3N_4$ 604A and a first layer of a metal (e.g., Au—Cr, Al, Graphene, etc.) or polysilicon layer 607A are deposited on top of each other. Then second and third layers of dielectric base, base, and metal 602B, 604B, 607B, 602C, 604C, 607C are deposited on top of each other and the previous layers. For instance, these deposition steps can be performed using chemical vapor deposition ("CVD") and/or Atomic Layer Deposition ("ALD") of base dielectric layers 602, trimming dielectric layers, and/or membrane dielectric layers (see FIG. 6C below). The first dielectric base layer 602A may have a thickness of about 100 nm to 1000 nm to reduce substrate coupled low level noise.

As shown in FIG. 6B, a nanopore 610 is then etched into the deposited layers (e.g., a using high aspect ratio (above 5) nanopore hole trench etching process). The high aspect ratio etching can provide a sharp shape to a trench profile of the nanopore 610 channel pillar. Total depth of the nanopore pillar can be few hundred nanometers to several microns depending on the applications.

Next, as shown in FIG. 6C, thin layers of a dielectric coating 612 (e.g., $Si_3N_4$, $Al_2O_3$, $SiO_2$, etc.) are deposited (e.g., by atomic layer deposition "ALD") on the inner surface of the nanopore 610 to determine the width of the nanopore 610. The dielectric coating 612 may vary in thickness (e.g., from about 10 nm to about 50 nm). By controlling the amount of dielectric coating 612 deposited on the inner surface of the nanopore 610 (e.g., using ALD) target nanopore 610 widths of about 2 nm to about 100 nm can be achieved. Accordingly, the width/diameter of the nanopore/trench 610 can be controlled using ALD of a dielectric coating 612 to suit a variety of applications. A top dielectric coating 612 may have a thickness of about 5 nm to about 20 nm. Depending on the applications and required nanopore 610 opening dimensions, various lithography techniques (e.g., those used in the mass volume production) can be used to etch the nanopore 610 opening. In addition, the depth of the nanopore 610 channel can be selected for the required sensitivity and accuracy with ease using the manufacturing methods described herein.

As shown in FIG. 6D, the vertical nanopore channel and the stacked layers are etched (see "steps" on right side of stacked layers) to form the horizontal (X axis) and vertical (Y axis) nanopore channels to provide access for electrodes

614 (e.g., row and column inhibitory electrodes) on top and addressing circuits. The base $Si_3N_4$ 604A (or $Al_2O_3$) layers are selectively wet etched to provide electrical access to all of the horizontal electrodes. Finally, the remaining space is filled with metal.

Figure 6E:
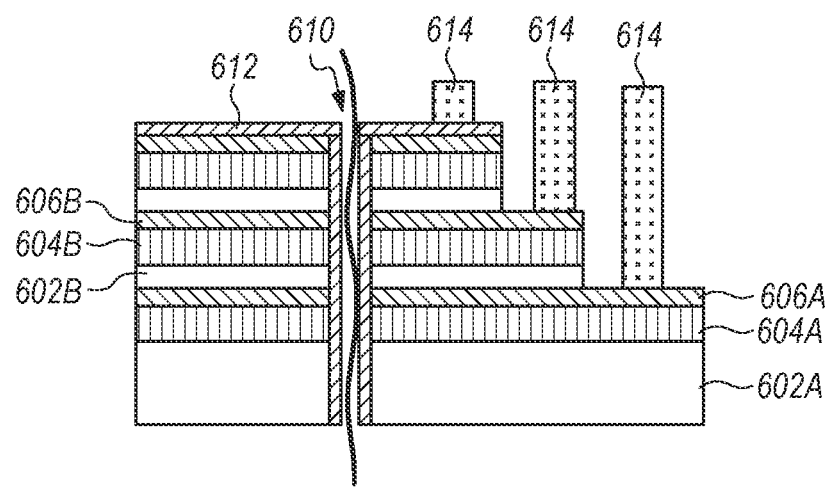

FIG. 6E depicts the manufactured 3D nanopore device in use for sequencing a biopolymer (e.g., DNA).

FIGS. 7A-7E illustrate a method 700 of manufacturing a nanopore device according to another embodiment. The methods 600, 700 depicted in FIGS. 6A-6E and 7A-7E are similar and share many of the same techniques.

As shown in FIG. 7A, multiple layers of dielectric films (such as $SiO_2$, $Al_2O_3$, ZnO, $HfO_2$, etc.; 10 nm-100 nm) low stress nitride film ($Si_3N_4$) and metal (Ta, Al, Cr, Ti, Au—Cr, Graphene, etc.; few nm to 100's of nm) and inter-metal layer ($SiO_2$) collectively 702 are stack deposited on a Si or Quartz substrate using CVD (Low Pressure/Plasma Enhanced) or Atomic Layer Deposition (ALD). Next, a bottom chamber opening 704 ($5 \times 5 \sim 100 \times 100$ μ$m^2$) is etched by a Deep Reactive Ion Etching (RIE) or KOH wet etching.

As shown in FIG. 7B, a top metal layer 706 is deposited. Next, a top chamber opening 708 is defined using a high aspect ratio nanopore hole deep trench etching process by Reactive Ion Etching. This process can generate nanopore trench etch opening diameters from a few nm to about 100 nm. Lithography techniques using colloidal mask (e.g., Nano-dots, Quantum-dots, or Graphene oxide pores) can also be used instead of conventional tools.

Figure 7D:
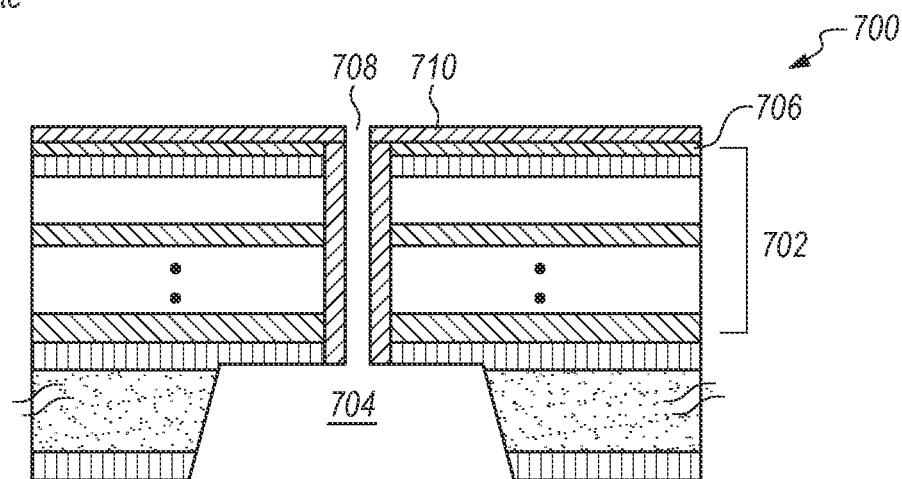

As shown in FIGS. 7C and 7D, Thin layers of dielectrics 610 (e.g., films) also can be deposited by ALD to trim the nanopore width to achieve target nanopore widths (using ALD) from about 2 nm to about 1000 nm. Nanopore channel widths can also be controlled to have variable trench width, allowing variable nanopore width for the target diameter.

Figure 7E:
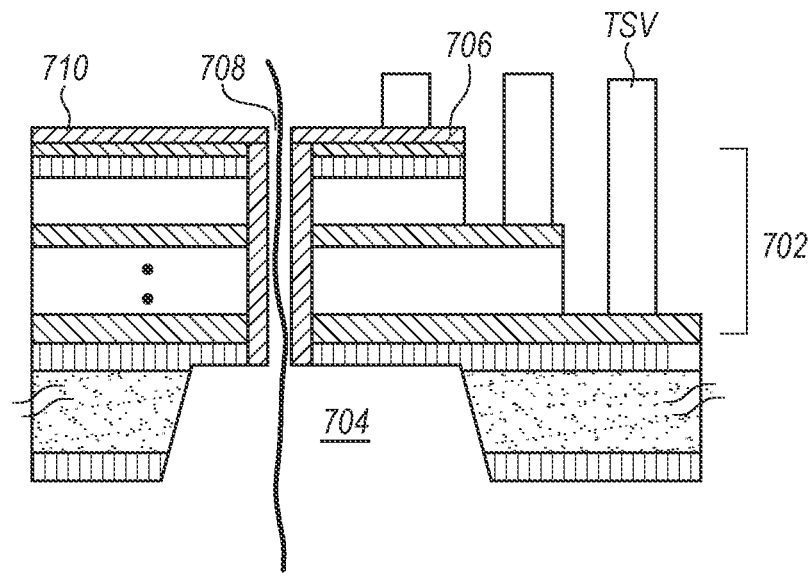

FIG. 7E depicts the manufactured 3D nanopore device in use for sequencing a biopolymer (e.g., DNA).

The 3D nanopore device may facilitate multiplex sequencing applications using high density low cost nanopore channels. A number of electrodes in the 3D nanopore device may be selected depending on the required sequencing applications to provide a Time of Flight ("TOF") technique to control the translocation speed by controlled biasing. Controlling the translocation speed may improve reading of DNA molecules and improves a sensitivity of the sensor. The 3D nanopore device may also facilitate an electro-chemical, thermal, or electro-optical reaction to take place in an enlarged, separated nanopore well with a multi-electrode system to enhance electrochemical and/or sequencing reactions. The 3D nanopore device may further facilitate multiplex sequencing using a multi-array configuration wherein individual nanopore channel pillars are addressable. Moreover, the 3D nanopore device may further facilitate standard qPCR within a nanopore channel pillar and/or probe-mediated targeted sequencing. In addition, the 3D nanopore channel opening width is tunable for different applications. In one embodiment, the nanopore channel opening width is tunable from about 1 nm to about 100 nm. The nanopore channel opening width may be electronically tunable during manufacturing. The 3D nanopore devices described herein can be used in the detection of various charged particles, including but not limited to biomolecules such as nucleotides, nucleic acids, and proteins (direct detection). The 3D nanopore devices can also be used in DNA sequencing and detection of protein-DNA interactions.

Manufacturing metal or polysilicon plane based nanopore arrays using lithographic processes (e.g., Through-Silicon Via ("TSV") fabrication) minimizes manufacturing cost and line resistance (which significantly reduces IR drop and RC delay limitations to scaling).

The corresponding structures, materials, acts and equivalents of all means or step plus function elements in the claims below are intended to include any structures, materials, acts and equivalents for performing the function in combination with other claimed elements as specifically claimed. It is to be understood that while the invention has been described in conjunction with the above embodiments, the foregoing description and claims are not to limit the scope of the invention. Other aspects, advantages and modifications within the scope to the invention will be apparent to those skilled in the art to which the invention pertains.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. Other details of the present invention, these may be appreciated in connection with the above-referenced patents and publications as well as generally known or appreciated by those with skill in the art. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A method of detecting a charged particle using a 3D nanopore device having top, middle, and bottom chambers, and a 3D nanopore array disposed in the middle chamber such that the top and bottom chambers are fluidly coupled by a plurality of nanopores in the 3D nanopore array, the method comprising:
    adding electrolyte solution including the charged particle to the top, middle, and bottom chambers;
    placing top and bottom electrodes in the top and bottom chambers respectively;
    applying an electrophoretic bias between the top and bottom electrodes;
    applying first and second selection biases to first and second selection electrodes in the 3D nanopore device to select one or more nanopores of the plurality of nanopores through which the charged particle will be directed;
    applying a rate control bias to a rate control electrode in the 3D nanopore device to modulate a translocation rate of the charged particle through the one or more nanopores;
    applying a sensing bias to a sensing electrode in the 3D nanopore device; and
    detecting a change in a current in the sensing electrode.

2. The method of claim 1, wherein the current is an electrode current.

3. The method of claim 1, wherein the current is a tunneling current.

* * * * *